United States Patent [19]

Hirschfeld

[11] Patent Number: 4,674,320

[45] Date of Patent: Jun. 23, 1987

[54] CHEMORESISTIVE GAS SENSOR

[75] Inventor: Tomas B. Hirschfeld, Livermore, Calif.

[73] Assignee: The United States of America as represented by the United States Department of Energy, Washington, D.C.

[21] Appl. No.: 781,543

[22] Filed: Sep. 30, 1985

[51] Int. Cl.[4] ............................................. G01N 27/12
[52] U.S. Cl. ......................................... 73/23; 338/34; 427/102
[58] Field of Search ................... 73/23, 27 R; 338/34, 338/35; 422/98; 324/71.5; 340/634; 427/102, 103

[56] References Cited

U.S. PATENT DOCUMENTS

| | | | |
|---|---|---|---|
| 3,676,188 | 7/1972 | Silverman et al. | 427/102 |
| 3,901,067 | 8/1975 | Boardman, Jr. et al. | 73/23 |
| 4,142,400 | 3/1979 | Colla et al. | 73/23 |
| 4,236,307 | 12/1980 | Colla et al. | 338/34 |
| 4,313,338 | 2/1982 | Abe et al. | 338/34 |
| 4,472,356 | 9/1984 | Kolesar Jr. | 422/98 |

OTHER PUBLICATIONS

B. Bott et al., "A Highly Sensitive $NO_2$ Sensor Based on Electrical Conductivity Changes in Phthalocyamine Films", *Sensors and Actuators*, vol. 5, pp. 43-53, 1984.

E. Hermans, "CO, $CO_2$, $CH_4$ and $H_2O$ Sensing by Polymer Covered Interdigitated Electrode Structures", *Sensors and Actuators*, vol. 5, pp. 181-186, 1984.

*Primary Examiner*—Stephen A. Kreitman
*Attorney, Agent, or Firm*—Bert J. Weis; Clifton E. Clouse, Jr.; Judson R. Hightower

[57] ABSTRACT

A chemoresistive gas sensor is provided which has improved sensitivity. A layer of organic semiconductor is disposed between two electrodes which, in turn, are connected to a voltage source. High conductivity material is dispersed within the layer of organic semiconductor in the form of very small particles, or islands. The average interisland spacing is selected so that the predominant mode of current flow is by way of electron funneling. Adsorption of gaseous contaminant onto the layer of organic semiconductor modulates the tunneling current in a quantitative manner.

11 Claims, 2 Drawing Figures

CHEMORESISTIVE GAS SENSOR

The U.S. Government has rights in this invention pursuant to Contract No. W-7405-ENG-48 between the U.S. Department of Energy and the University of California, for the operation of the Lawrence Livermore National Laboratory.

BACKGROUND OF THE INVENTION

The invention relates generally to gas sensing apparatus, and more particularly to gas sensing apparatus utilizing the adsorbent properties of organic semiconductors.

There is pressing need for highly selective and sensitive detectors of gaseous constituents in a wide variety of industrial, medical, and military contexts. There is a need to detect and monitor contaminant gases in industrial purification processes; anesthetic gases in operating rooms; chemical warfare agents on the battlefields; and environmental pollutants in industrial or agricultural areas.

Many of the current approaches to contaminant gas detection lack sensitivity and selectivity. For example, the selectivity of individual piezoelectric sorption detectors of the type disclosed by King, Jr., U.S. Pat. Nos. 3,164,004 or by Frechette et al, 4,111,036, depends entirely on the selectivity of the adsorbent coatings on the piezoelectric crystals. The selectivity of these adsorbent materials are notoriously poor, e.g., Hirschfeld, "Providing Innovative System Monitoring and Reliability Assessment Through Microengineering", *Energy Technology and Review*, February 1984; and Edwards et al, "A Quartz Crystal Piezoelectric Device for Monitoring Organic Gaseous Pollutants", *Analytica Chimica Acta*, Vol. 117, pgs. 147-157 (1980). Selectivity problems can be overcome to a large extent by employing a plurality of sensors each having a different adsorbent coating. The responses of the multiple sensors are analyzed by factor analysis or least squares analysis to obtain information about the concentrations of contaminants in the gas being monitored.

Another approach to detecting contaminant gases utilizes their effects on the conductivities of certain organic semiconductors. The class of sensors based on this approach is referred to as chemoresistive gas sensors. A thin layer of organic semiconductor is disposed on a surface between two electrodes. The layer of organic semiconductor is exposed to the atmosphere containing the contaminant gases of interest. As the organic semiconductor adsorbs the contaminant gases, its conductivity changes, and the magnitude of the change is related to the concentration of contaminant gas. The following references provide representative disclosures of such gas detection systems: Colla et al, U.S. Pat. Nos. 4,142,400 and 4,236,307; Kolesar, 4,472,356; Bott et al, "A Highly Sensitive $NO_2$ Sensor Based on Electrical Conductivity Changes in Phthalocyanine Films", *Sensors and Actuators*, Vol. 5, pgs. 43-53 (1984); and Hermans, "CO, $CO_2$, $CH_4$, and $H_2O$ Sensing by Polymer Covered Interdigitating Electrode Structures", *Sensors and Actuators*, Vol. 5, pgs. 181-186 (1984). Like the piezoelectric-based sensors, the selectivity of chemoresistive sensors is limited by the lack of selectivity of the organic semiconductors for particular gaseous contaminants. This class of sensor is also limited by the extremely low conductivity of the layers of organic semiconductor, which is on the order of $10^{-10}$–$10^{-8}$ ohms$^{-1}$. The low conductivity means that the changes introduced by the adsorbed contaminants will be correspondingly low and difficult to detect; hence, the sensitivity of the system is low.

SUMMARY OF THE INVENTION

An object of the invention is to provide a sensor for gaseous contaminants with improved selectivity and sensitivity.

Another object of the invention is to improve the sensitivity of chemoresistive gas sensors.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

These and other objects are attained in accordance with the present invention by enhancing the conductivity of the organic semiconductor layers used in chemoresistive gas sensors. Chemically inert, high conductivity materials are embedded in the organic semiconductor layer such that islands of high conductivity material are dispersed throughout the layer at a predetermined average interisland spacing. The average interisland spacing is selected so that the predominant path of current flow is by way of electron tunneling between the islands of high conductivity material. The magnitude of the tunneling current depends on the nature of the high conductivity material, the nature of the organic semiconductor, the average distance between the islands of high conductivity material, the average size of the islands, the voltage across the layer of organic semiconductor, and the amount of gaseous contaminants adsorbed onto the organic semiconductor. In accordance with the invention, all of the above factors are predetermined, except the amount of gaseous contaminants adsorbed onto the organic semiconductor.

Preferably, the layer of organic semiconductor together with the embedded islands of high conductive material is placed on a nonconductive substrate having good thermal conductivity. Good thermal conductivity allows the temperature of the layer of organic semiconductor to be controlled so that temperature-dependent changes in conductivity can be eliminated, or minimized.

DETAILED DESCRIPTION OF THE INVENTION

The invention is a chemoresistive gas sensor with increased sensitivity, and method for making same. The increased sensitivity is attained by modifying a layer of organic semiconductor so that it contains islands of high conductivity material. The average interisland spacing is selected so that the predominant current path through the layer is by way of electron tunneling between the islands. The presence of the islands in accordance with the invention increases the conductivity of the chemosensitive layer by two to three orders of magnitude, and thereby causes corresponding increases in the variances in current due to gaseous contaminants being adsorbed onto or expelled from the layer of organic semiconductor.

Figure 1:
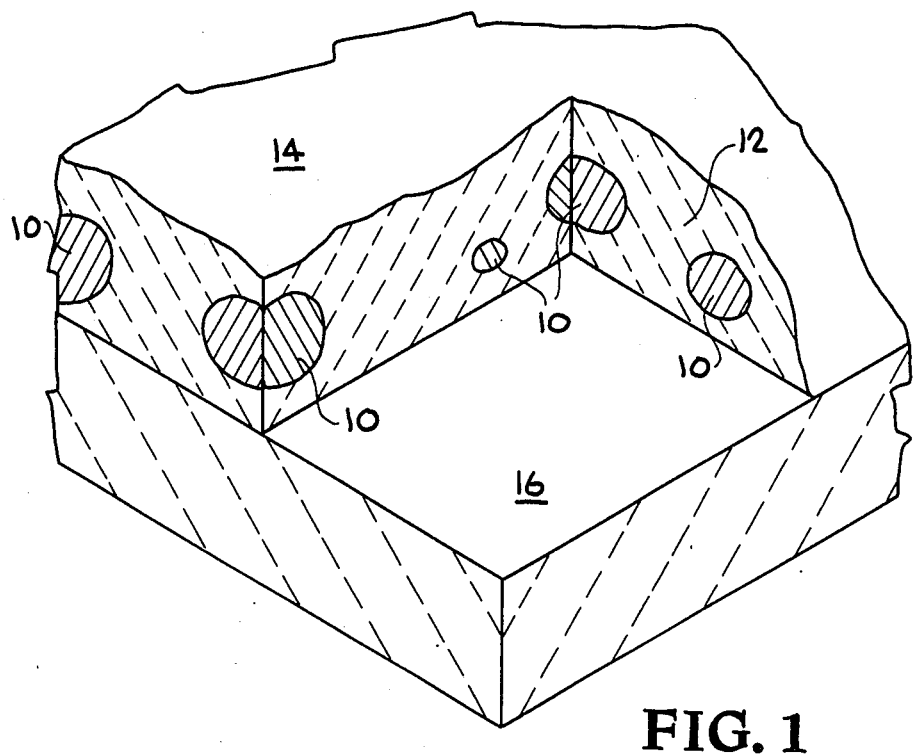
FIG. 1 is a cutaway view of the layer of organic semiconductor on a substrate that exposes the islands of high conductivity material.

FIG. 1 presents a cutaway view of a layer of organic semiconductor which illustrates how the islands of high conductivity material are embedded in the layer. In this embodiment, islands 10 of high conductivity material are covered by and embedded in organic semiconductor 12 to form chemoresistive layer 14 on substrate 16.

Figure 2:
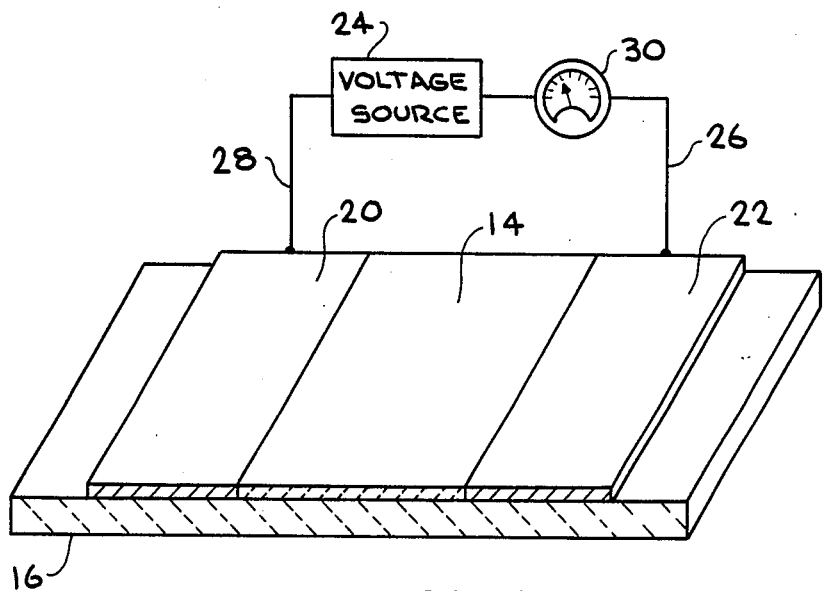
FIG. 2 is an illustration of an embodiment of the invention employing a single layer of organic semiconductor.

FIG. 2 illustrates an embodiment of the invention employing a single kind of organic semiconductor. Chemoresistive layer 14 is disposed between electrodes 20 and 22 on substrate 16. Electrodes 20 and 22 are connected to voltage source 24 by leads 26 and 28. The current passing through the chemoresistive layer is monitored by meter 30.

A critical parameter of the chemoresistive layer is the average interisland spacing of high conductivity material. Preferably, the average interisland spacing is between about 10-80 Angstroms. Most preferably, the average interisland spacing is between about 50-60 Angstroms.

Several organic semiconductors are suitable for use with the present invention including phthalocyanine and its derivatives (disclosed in Moser et al, in *Phthalocyanine Compounds* (Van Nostrand, New York, 1963); electrically conductive acetylene polymers (disclosed in U.S. Pat. Nos. 4,510,075 and 4,510,076); polymeric semiconductors disclosed in U.S. Pat. No. 4,472,356; and the like. The three cited U.S. patents are incorporated by reference to their disclosures of organic semiconductors. The preferred organic semiconductor is phthalocyanine and its derivatives, particularly its halogenated or sulfonated derivatives.

The substrate to which the chemoresistive layer is attached is nonconductive electrically, but preferably it has good heat conductivity. A preferred substrate material is sapphire.

Referring to FIG. 2, the preferred embodiment of the invention is constructed by depositing a continuous thin film of high conductivity material on the substrate surface between electrodes 20 and 22. Preferably, the high conductivity material is gold. The thin film is preferably between about 100-300 Angstroms thick, and is deposited by standard metal deposition techniques. The substrate material with the continuous thin film coating is then heated to a temperature high enough for the thin film to form mobile droplets on the surface of the substrate. At this temperature, the droplets move around on the surface of the substrate and coalesce when they come into contact with one another. when the droplets cool and solidify, they form the islands of high conductivity material. By maintaining the substrate at the elevated temperature, one can adjust the average interisland spacing. The longer the droplets are allowed to move about and coalesce, the larger the average interisland spacing tnat will result. The shorter the time, the smaller the average interisland spacing. The precise temperature required, and the length of time for which it is maintained in order to achieve a desired average interisland spacing, requires some testing for the particular materials used. Preferably, the surface of the substrate on which the chemoresistive layer rests is optically smooth. That is, it is smooth enough so that droplet formation occurs, and there are no sizable grooves, cracks, or other irregularities which could cause the formation of channels of high conductivity material upon cooling. Such a condition is undesirable because the channels would provide alternative current pathways to electron tunneling.

When the high conductivity material is gold, and it is deposited as a continuous 100-300 Angstrom film on the surface of the substrate, the preferred temperature for formation of droplets is between about 150°-200° C.

Preferably, the organic semiconductor is deposited on the solidified islands by sublimation under a vacuum in order to avoid impurities in the chemoresistive layer, e.g., by the method disclosed by Bott et all, *Sensors and Actuators*, Vol. 5, pgs. 43-53 (1984), or like method. Preferably the thickness of the layer of organic semiconductor is on the order of the average diameter of the islands of high conductivity material. Thicker layers reduce the response time of the sensor; thinner layers may in.troduce undesirable complications because of inhomogeneities in the material between islands.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

I claim:

1. An apparatus for sensing gaseous contaminants, the apparatus comprising:
   a layer of organic semiconductor on a surface of an associated substrate material, the associated substrate material being nonconductive;
   a first electrode and a second electrode attached to the layer of organic semiconductor at spaced locations on the surface of the associated substrate material, the first electrode and second electrode being connected to an associated voltage source; and
   a plurality of islands of high conductivity material dispersed within the layer of organic semiconductor, the plurality of islands having an average interisland spacing such that a detectable amount of current traverses between the first electrode and the second electrode by electron tunneling between tne islands of high conductivity material.

2. The apparatus of claim 1 wherein said average interisland spacing is between about 10-80 Angstroms.

3. The apparatus of claim 2 wherein said high conductivity material is gold.

4. The apparatus of claim 3 wherein said organic semiconductor is selected from the group consisting of phthalocyanine, halogenated phthalocyanine, and sulfonated phthalocyanine.

5. The apparatus of claim 4 wherein said organic semiconductor is phthalocyanine.

6. The apparatus of claim 5 wherein said average interisland spacing is between about 50-60 Angstroms.

7. The apparatus of claim 6 wherein said associated substrate material is sapphire.

8. A method of constructing a chemoresistive gas sensor, the method comprising the steps of:

depositing a layer of high conductivity material on a surface of an associated substrate material, the associated substrate material being nonconductive;

heating the layer of high conductivity material so that mobile droplets of the high conductivity material form on the surface of the associated substrate;

cooling the associated substrate material so that the mobile droplets of high conductivity material solidify to form islands;

depositing a layer of organic semiconductor over the islands of high conductivity material on the surface of the associated substrate material; and attaching electrical electrodes to the layer of organic semiconductor at spaced locations.

9. The method of claim 8 wherein said layer of high conductivity material is between about 100–300 Angstroms thick.

10. The method of claim 9 wherein said high conductivity material is gold and said organic semiconductor is phthalocyanine.

11. The method of claim 10 wherein said step of heating includes raising the temperature of said associated substrate material to between about 150°–200° C.

* * * * *